(12) United States Patent
Krull et al.

(10) Patent No.: US 7,014,810 B2
(45) Date of Patent: Mar. 21, 2006

(54) METHOD OF PRODUCING SOLID SHAPE FORMS CONTAINING AN ACTIVE INGREDIENT

(75) Inventors: Harald Krull, Ludwigshafen (DE); Jörg Rosenberg, Ellerstadt (DE); Jörg Breitenbach, Mannheim (DE); Jürgen Hofmann, Ludwigshafen (DE); Rainer Klenz, Hassloch (DE); Hans Bührle, Limburgerhof (DE)

(73) Assignee: Abbott GmbH & Co. KG, Wiesbaden (DE)

(*) Notice: Subject to any disclaimer, the term of this patent is extended or adjusted under 35 U.S.C. 154(b) by 12 days.

(21) Appl. No.: 10/149,762

(22) PCT Filed: Dec. 15, 2000

(86) PCT No.: PCT/EP00/12797

§ 371 (c)(1), (2), (4) Date: Jun. 13, 2002

(87) PCT Pub. No.: WO01/43943

PCT Pub. Date: Jun. 21, 2001

(65) Prior Publication Data

US 2003/0015814 A1    Jan. 23, 2003

(30) Foreign Application Priority Data

Dec. 15, 1999 (DE) ................................ 199 60 494

(51) Int. Cl.
*B29C 45/03* (2006.01)
*B29C 45/72* (2006.01)

(52) U.S. Cl. ............................ 264/328.4; 264/328.14; 425/547; 425/548; 425/552

(58) Field of Classification Search ................ 425/557, 425/560, 567, 572, 559, 574, 812, 130, 549, 425/547, 548, 552; 264/266, 268, 328.14, 264/328.4
See application file for complete search history.

(56) References Cited

U.S. PATENT DOCUMENTS

| | | | | |
|---|---|---|---|---|
| 3,417,433 A | * | 12/1968 | Teraoka ...................... | 425/559 |
| 4,379,103 A | * | 4/1983 | Doerfling .................... | 425/812 |
| 4,738,817 A | * | 4/1988 | Wittwer et al. ........ | 264/328.14 |
| 4,808,101 A | * | 2/1989 | Schad et al. ................ | 425/130 |
| 4,994,226 A | * | 2/1991 | Nakagawa et al. ......... | 264/266 |
| 5,324,190 A | * | 6/1994 | Frei ........................... | 425/549 |
| 5,833,899 A | * | 11/1998 | Wunderlich ................ | 425/130 |
| 5,885,691 A | * | 3/1999 | Breezer et al. ............. | 264/268 |

* cited by examiner

*Primary Examiner*—Tim Heitbrink
(74) *Attorney, Agent, or Firm*—Novak Druce & Quigg LLP; Jason D. Voight (57) ABSTRACT

The present invention relates to an apparatus for producing solid active ingredient-containing forms from an active ingredient-containing formulation which comprises at least one polymeric binder. The apparatus according to the invention has at least one extruder 1 for continuous plastication of the formulation and at least two injection units 2 which are provided separate from one another, each of which is connected to the extruder 1, and through which the formulation can be injected into at least one mold 3. In the process according to the invention for producing solid active ingredient-containing forms from an active ingredient-containing formulation which comprises at least one binder, the active ingredient-containing formulation is continuously plasticated, the plasticated formulation is fed into an injection unit $2_1$, and the formulation present in this injection unit $2_1$ is injected into a mold 3, and plasticated formulation is fed into another injection molding unit $2_2$, and the formulation present in the other injection molding unit $2_2$ is injected into the mold 3 or another mold.

4 Claims, 6 Drawing Sheets

METHOD OF PRODUCING SOLID SHAPE FORMS CONTAINING AN ACTIVE INGREDIENT

The present invention relates to an apparatus for producing solid active ingredient-containing forms from an active ingredient-containing formulation which comprises at least one polymeric binder, having at least one extruder for continuous plastication of the formulation. The invention further relates to a process for producing solid active ingredient-containing forms from such a formulation.

The solid pharmaceutical forms described above are conventionally produced by initially preparing an active ingredient-containing formulation by means of a melt extrusion process and then carrying out the shaping. In the shaping, the solid forms are produced, for example by means of counter-rotating blender rolls, from the active ingredient-containing melt obtained in the extrusion. An apparatus of this type is described in WO 97/15268.

In addition, forms are produced in plastics technology by injection molding. These apparatuses and processes known from plastics processing cannot, however, be directly employed for producing active ingredient-containing forms. This is because, in contrast to the continuously operating process on use of calendering, it is necessary on use of the injection molding process for part of the processing step to take place discontinuously because the melt is forced under high pressure into shaped cavities and must cool there before the cavities of the mold can be charged again with a new melt. This has disadvantageous effects on the production of active ingredient-containing forms because the residence times of the active ingredient-containing melt at the high temperatures necessary to produce the melt are very much longer than in the case of the calendering process, in which the melt is conveyed continuously without interruption into the molding calender. The long residence times of the melt in the extruder until the cooling in the mold cavities lead in the case of sensitive active ingredients to the formation of considerable proportions of decomposition products, which must not occur in active ingredient-containing forms.

EP 240 904 B1 refers to the injection molding technique in connection with a process for producing solid active ingredient-containing forms, but no further information is given therein as to how an apparatus or a process could be designed in detail to make it possible to avoid the above disadvantages.

It is an object of the present invention to indicate an apparatus and a process for producing solid active ingredient-containing forms, in which there is use of the injection molding technique but the disadvantages associated therewith are avoided.

We have found that this object is achieved by an apparatus as described herein.

The apparatus according to the invention has at least two injection units which are provided separate from one another and each of which is connected to the extruder and through which the formulation can be injected into at least one mold.

The provision of at least two injection units which are provided separate from one another in the apparatus according to the invention advantageously prevents the active ingredient-containing formulation remaining too long in the extruder in which the temperatures prevailing for the plastication of the formulation are so high that, if the residence times of the formulation in the extruder are lengthy, decomposition parts are formed. The plasticated active ingredient-containing formulation can reach an injection unit very much faster with the apparatus according to the invention, because it is always possible to charge the injection unit which is just not injecting any formulation into a mold. The apparatus according to the invention thus combines the extruder which can be operated continuously with a plurality of discontinuously operating injection units, avoiding the disadvantages resulting from the discontinuities. This additionally increases the rate of production of the active ingredient-containing forms. It is possible in particular in the injection molding of active ingredient-containing forms with a short cooling time and high shot weights or large numbers of items, such as, for example, in the case of tablets, that the efficiency of the active ingredient-containing forms is increased considerably. It is possible with the apparatus according to the invention to achieve very high production rates of up to 400 000 active ingredient-containing forms per hour. The usual production rates for the apparatus according to the invention are more than 50 000 items per hour and advantageously between 100 000 and 300 000 items per hour. The weights of the active ingredient-containing forms are normally between 50 and 2000 mg, but usually between 150 and 1300 mg.

In addition, the melt quality is increased in an extruder which can be operated continuously by comparison with an extruder which can only be operated discontinuously, because the plastication conditions, such as the extruder screw speed, the temperature, the plasticating screw length and the output, remain constant.

In an advantageous embodiment of the present invention it is possible for at least one injection unit to be connected to a plurality of molds which are arranged in parallel and into which the formulation can be injected simultaneously. It is additionally possible for at least one injection unit to be connected to a plurality of molds which can be coupled singly to the injection unit and into which the formulation can be injected successively. A further possibility is for a plurality of injection units to be capable of alternate coupling to a mold. If the melt plastication is the rate-determining step, this embodiment makes it advantageously possible to increase the rate of production of the active ingredient-containing form.

If the injection molding process is the rate-determining step, for example in the production of small active ingredient-containing forms with long cooling times, the rate of production can be increased by providing a plurality of molds per injection unit.

In a further embodiment, the mold(s) is/are designed as multi-daylight molds with in each case a plurality of individual molds. It is also possible with this embodiment advantageously to increase the rate of production if it is intended to produce small active ingredient-containing forms with relatively long cooling times.

In another embodiment according to the invention, in each case the volume of one cylinder of an injection unit corresponds to the volume of the mold or of the molds into which the formulation can be injected by the particular injection unit.

Since in this embodiment all the formulation present in the injection unit is ejected in each injection process there is advantageous avoidance of a hot active ingredient-containing formulation remaining in an injection unit for too long, so that either the active ingredient or the polymeric binder may decompose. This additionally minimizes the time between the filling of the cylinder and the injection into the mold.

In another embodiment according to the invention, an accumulator unit is provided between the extruder and the injection units for temporary storage of the formulation continuously produced by the extruder and for conveying the formulation to the discontinuously operated injection units. Although this design results in a somewhat increased time from the extrusion to the injection process, it is possible in this way to ensure continuous operation of the extruder in every case. The continuous procedure results in an improvement in the properties of the plasticated formulation.

The use of an accumulator unit additionally makes it possible to connect the continuously operating extruder to only one discontinuous injection unit, because the temporary store decouples the extruder and the injection unit. The decoupling makes continuous plastication in the extruder possible.

In another embodiment according to the invention there is provided between the extruder and the injection units a feed valve into which the formulation plasticated by the extruder can be fed and through which the formulation fed in can be distributed to the injection units. The provision of the feed valve ensures decoupling of continuously operated extruder from the discontinuously operated injection units.

In another embodiment of the apparatus according to the invention, the latter has a plurality of extruders for continuous plastication of different compositions, at least one composition being the active ingredient-containing formulation, and the plurality of extruders each being connected to one or more injection units, and a mold being connected to at least two injection units into which compositions can be fed from various extruders. It is advantageous in this case for the mold to be designed as the female mold of an active ingredient-containing form to be produced, the active ingredient-containing form having essentially the shape of a hemisphere with a cavity or of a hollow hemicylinder. It is also possible in this case for the compositions to be fed to the mold by the injection units in such a way that the produced form can release the active ingredient only across the surface of the inner wall of the hollow sphere or of the hollow cylinder.

This embodiment makes a multicomponent injection molding possible. This may entail, for example, a form being produced from two or more different active ingredient-containing formulations which contain one or more active ingredient(s), in which case it is possible to produce successive layers with different formulations. It is possible in this way, for example, to produce active ingredient-containing forms with a multiphase release profile or a 0 order release profile, the latter being of particular interest. Whereas with conventional active ingredient-containing forms such as, for example, tablets there is a decrease in the release of active ingredient per unit time, which depends essentially on the surface area of the form (non-0 order release of active ingredient), because of the reduction in the surface area with increasing dissolution of the form, it is possible by multicomponent injection molding to produce forms which have a constant release of active ingredient per unit time (0 order release of active ingredient) because of the constancy of the active ingredient-releasing surface area. Forms displaying 0 order release of active ingredient have already been described by W. D. Rhine et al., in "Controlled Release of Bioactive Materials", Academic Press, 1980, ISBN 0-12-074450-3.

A further possibility with multicomponent injection molding is direct coating of the active ingredient-containing forms with diverse formulations, it also being possible for these formulations to contain active ingredients.

In another embodiment of the apparatus according to the invention, the extruder(s) is/are (a) twin screw extruder(s). Twin screw extruders are defined herein as extruders with two screws which are located side by side and which rotate in the opposite or same direction. The advantage of using twin screw extruders by comparison with single screw extruders is that they are particularly suitable for processing the active ingredient-containing starting materials. These starting materials or mixtures of materials for active ingredient-containing forms are almost always in powder form, which leads to the apparent density being considerably lower than that of plastic granules. This leads to problems in charging if extruders used in plastics processing are used to produce the active ingredient-containing forms. Twin screw extruders have essentially better properties than single screw extruders when fed with mixtures of substances in the form of low density powders. This leads to a considerably better melt flow in the extruder. In addition, on use of single screw extruders, the active ingredient-containing formulation to be melted must be granulated beforehand in order to increase the apparent density. This is advantageously no longer necessary on use of twin screw extruders.

The injection molding units used are advantageously at least in part plunger injection units. It is possible with such plunger injection units to ensure, better than with screw injection units, that no active ingredient-containing formulation remains in the plunger after the injection process and, in this case, there is decomposition of the active ingredient or the polymeric binder.

In another preferred embodiment according to the invention, the injection units and the molds are connected by temperature-controllable hot runner systems. The advantage of using hot runner systems is that the plasticated composition solidifies only in the actual mold cavities of the injection mold but not in the melt feed channels. It is possible in this way, especially when injecting small molds, to increase the yield considerably, because there is no sprue, which is otherwise produced, and thus production is virtually free of waste. Another advantage is a shortening of the cycle time and thus an increase in the production rates, because there is no cooling of sprue, which usually determines the cycle time.

The hot runner technique plays an important part in the economic production of active ingredient-containing forms by means of injection molding, because the use thereof reduces the waste of active ingredients, which are usually costly, to a minimum and, because there is no sprue, the cycle time can be noticeably reduced, which is associated with an increase in the production rates.

The hot runner systems consist of a feed region and hot runner nozzles which contain injection channels for injecting the compositions into the cavities of the mold. To produce active ingredient-containing forms the temperatures set in the hot runner systems are preferably between 50 and 250° C., particularly preferably between 100 and 200° C.

The temperature in the hot runner can be controlled by means of a fluid or of an electrical heating system, with the countercooling unit advantageously being provided in the latter case.

Irrespective of the use of a hot runner system, it is also possible for the temperatures of the injection units, which are usually electrically heated, the outlet opening of the extruder and/or the feed valve to be controlled by means of a heating-cooling fluid.

A problem occurring with apparatuses for producing solid active ingredient-containing forms from an active ingredient-containing formulation in which there is use of the injection molding technique is that rises in temperature which harm the active ingredient-containing formulation may occur during plastication of the formulation and during injection of the latter into a mold. The active ingredient-containing formulation is heated by the plastication process in the extruder and is injected through the injection unit into the mold. During this the temperature of the formulation is increased through compression and through the mold-filling process because of internal friction. These disadvantageous increases in temperature can be counteracted by the provision of a temperature control system in the apparatus according to the invention.

If an electrical temperature control system is used it is possible to prevent an overheating of the formulation because of compression and internal friction during the injection process through installation of a countercooling.

Control of temperatures by means of a heating-cooling fluid is particularly effective because it is possible to prevent both overheating of the formulation through compression and internal friction, and the local overheating of the formulation occurring with electrical heating systems, because of the more uniform transfer of heat between fluid and formulation in contrast to electrical heating systems.

It is possible according to the invention for the apparatus described above to be used in particular for producing active ingredient-containing forms with 0 order active ingredient release. A further possibility is to use it to produce active ingredient-containing forms with a multiphase release profile.

In the process according to the invention for producing solid active ingredient-containing forms from an active ingredient-containing formulation which comprises at least one polymeric binder there is continuous plastication of the active ingredient-containing formulation, and the plasticated formulation is fed into an injection unit and from there injected into a mold. The plasticated formulation is also fed into another injection unit and from there injected into a mold. The various injection units may inject the formulation successively into the same mold or into different molds. It is advantageous for the volume of formulation fed into one injection unit to correspond to the volume injected into the mold.

In one embodiment of the process according to the invention, the plasticated formulation is temporarily stored and then fed into an injection unit.

In another embodiment, different compositions can be injected into a mold, in which case at least one composition contains an active ingredient-containing formulation. It is also possible to place two sheets in the mold before the injection, between which the formulation is injected.

The active ingredient-containing formulation can also be mixed and/or homogenized before the injection, for example during the plastication. A further possibility is to control the temperature of the formulation during injection, during plastication, during feeding and/or during temporary storage.

A suitable polymeric binder is used according to the invention to produce the active ingredient-containing form. The binder may be swellable or soluble in water.

Binders which can be used according to the invention are polyvinyllactams, in particular polyvinylpyrrolidone (PVP), copolymers of vinyllactams such as N-vinylpyrrolidone, N-vinylpiperidone and N-vinyl-ε-caprolactam, but especially N-vinylpyrrolidone, with (meth)acrylic acid, (meth) acrylic esters, vinyl esters, especially vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates, copolymers of dimethylaminoethyl acrylates and methacrylic esters (for example Eudragit types), polyalkylene glycols such as polypropylene glycols and polyethylene glycols (for example polyethylene glycol 6000), copolymers of methyl methacrylate and acrylic acid, cellulose esters, cellulose ethers, especially methylcellulose and ethyl cellulose, hydroxyalkylcelluloses, in particular hydroxypropylcellulose or hydroxypropylmethylcellulose, hydroxyalkylalkylcelluloses, especially hydroxypropylethylcellulose, cellulose phthalates, especially cellulose acetate phthalate and hydroxypropylmethylcellulose phthalate, and mannans, especially galactomannans.

It is also possible to use gelatin and biodegradable polymers such as polyhydroxy alkanoates, for example polyhydroxybutyric acid, polylactic acid, polyamino acids, for example polylysine, polyasparagine, polydioxanes and polypeptides.

Preferred polymeric binders are polyvinylpyrrolidone, copolymers of N-vinyllactams, especially N-vinylpyrrolidone, and vinyl esters, copolymers of N-vinyllactams, especially N-vinylpyrrolidone, with (meth)acrylic esters, poly (hydroxyalkyl acrylates), poly(hydroxyalkyl methacrylates), polyacrylates, polymethacrylates, alkylcelluloses and hydroxyalkylcelluloses.

An advantage of the process according to the invention is that it is suitable for binders of widely varying viscosity, for example for binders with K values (according to H. Fikentscher, Cellulose-Chemie 13 (1932), pp. 58–64 and 71–74) between 10 and 100, in particular between 20 and 100. The advantages of this process are particularly evident with binders having a K value of >45 and preferably of >50.

Besides the polymeric binder, the formulation may contain conventional additives such as plasticizers, pharmaceutical excipients such as lubricants, release agents, flowability agents, dyes, stabilizers etc.

Examples of such plasticizers are:

long-chain alcohols, ethylene glycol, propylene glycol, glycerol, trimethylolpropane, triethylene glycol, butanediols, pentanols such as pentaerythritol, hexanols, polyethylene glcyols, polypropylene glycols, polyethylene/propylene glycols, silicones, aromatic carboxylic esters (for example dialkyl phthalates, trimellitic esters, benzoic esters, terephthalic esters) or aliphatic dicarboxylic esters (for example dialkyl adipates, sebacic esters, azelaic esters, citric and tartaric esters), fatty acid esters, such as glycerol mono-, di- or triacetate or sodium diethyl sulfosuccinate. The concentration of plasticizer is generally from 0.5 to 15, preferably 0.5 to 5, % by weight based on the total weight of the mixture.

Conventional pharmaceutical excipients, whose total amount can be up to 100% by weight based on the polymer, are, for example, extenders and bulking agents such as silicates or diatomaceous earth, magnesium oxide, aluminum oxide, titanium oxide, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % by weight, based on the total weight of the mixture;

lubricants and release agents such as magnesium, aluminum and calcium stearates, talc and silicones, and animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, especially lecithin. The mono- and diglycerides are preferably derived from the abovementioned fatty acid types. The total amount of lubricants and release agents is preferably from 0.1 to 5% by weight, based on the total weight of the composition for each layer;

flowability agents, for example Aerosil, in an amount of from 0.1 to 5% by weight, based on the total weight of the mixture;

dyes such as azo dyes, organic or inorganic pigments or dyes of natural origin, with preference for inorganic pigments in a concentration of from 0.001 to 10, preferably 0.5 to 3, % by weight, based on the total weight of the mixture;

stabilizers such as antioxidants, light stabilizers, hydroperoxide destroyers, radical scavengers, stabilizers against microbial attack.

It is also possible to add wetting agents, preservatives, disintegrants, adsorbents, mold release agents and blowing agents (cf., for example, H. Sucker et al., Pharmazeutische Technologie, Thieme-Verlag, Stuttgart 1978).

Excipients include for the purpose of the invention substances for producing a solid solution with the active ingredient. Examples of these excipients are pentaerythritol and pentaerythritol tetraacetate, polymers such as, for example, polyethylene oxides and polypropylene oxides and block copolymers thereof (poloxamers), phosphatides such as lecithin, homo- and copolymers of vinylpyrrolidone, surfactants such as polyoxyethylene stearate, and citric and succinic acid, bile acids, sterols and others as indicated, for example, in J. L. Ford, Pharm. Acta Helv. 61, (1986), 69–88.

Excipients are also regarded as being additions of bases and acids to control the solubility of an active ingredient (see, for example, K. Thoma et al., Pharm. Ind. 51, (1989), 98–101).

The only precondition for the suitability of excipients is adequate thermal stability.

Active ingredients for the purpose of the invention are all substances with a biological effect, such as, for example, active pharmaceutical ingredients, but also vitamins and minerals, and plant treatment agents and insecticides.

The active ingredients must undergo negligible decomposition under the processing conditions. The amount of active ingredient per dose unit and the concentration may vary within wide limits depending on the activity and rate of release. The only condition is that they suffice to achieve the desired effect. Thus, the active ingredient concentration can be in the range from 0.001 to 95, preferably from 20 to 80, in particular 30 to 70, % by weight. It is also possible to employ combinations of active ingredients. The vitamins include the vitamins of the A group, of the B group, by which are meant besides $B_1$, $B_2$, $B_6$ and $B_{12}$ and nicotinic acid and nicotinamide also compounds with vitamin B properties such as, for example, adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides and vaccines.

The process according to the invention is suitable, for example, for processing the following active ingredients or pharmacologically active salts thereof:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazoline, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, itraconazole, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine, captopril, omeprazole, ranitidine, tramadol, cyclosporin, trandolapril and therapeutic peptides.

It is possible in particular for solid solutions to be formed. The term "solid solutions" is familiar to the skilled worker, for example from the literature cited at the outset. In solid solutions of active ingredients in polymers, the active ingredient is in the form of a molecular dispersion in the polymer.

The weight of the active ingredient-containing forms produced is preferably between 50 mg and 2000 mg, particularly preferably between 150 mg and 1300 mg.

The process according to the invention has the same advantages as the apparatus according to the invention. In particular, it is possible with the process according to the invention for the active ingredient-containing formulation to be plasticated continuously and, at the same time, for the active ingredient-containing form to be produced by an injection process. This is made possible by the fact that the plasticated formulation is not injected directly into a mold or fed to only one injection unit, but to at least two injection units.

The invention is now explained in detail by means of examples with reference to the following drawings.

FIG. 4a shows 0 order and non-0 order active ingredient release profiles.

The apparatus according to the invention is used to produce solid active ingredient-containing forms which comprise an active ingredient-containing formulation which comprises a suitable polymeric binder which is, for example, soluble or swellable in water. The starting materials for the formulation are fed, for example, as powdered materials or mixtures of materials into an extruder 1. The introduced formulation is continuously plasticated in the extruder, i.e. converted into a sufficiently free-flowing state. This normally takes place by heating the formulation present in extruder 1. In addition, the starting materials are mixed and homogenized in extruder 1.

Extruder 1 can be, for example, a twin screw extruder which has two screws which are side by side and which rotate in the opposite or same direction. Extruder 1 may also be a multiscrew extruder, a kneader, a twin screw or multiscrew extruder with melt pump, a twin screw or multiscrew extruder with degassing device or a planetary gear extruder. In some circumstances, it would also be possible to use a single screw extruder, but in this case only limited processing of powder mixtures is possible.

Figure 1:
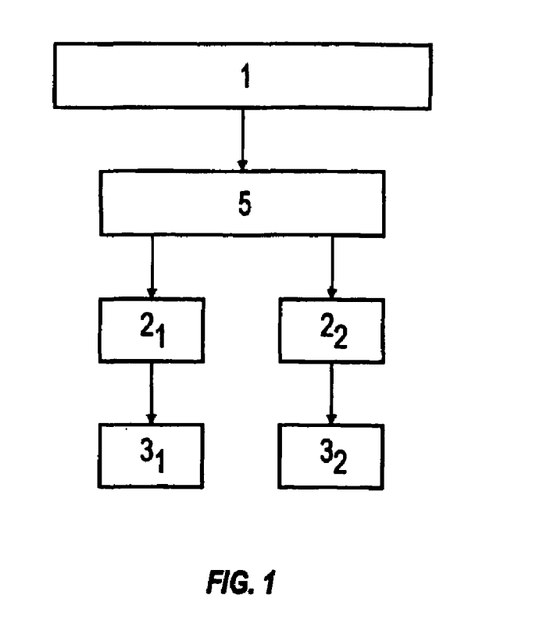
FIG. 1 shows a particularly preferred embodiment of the apparatus according to the invention.

In the embodiment shown in FIG. 1, extruder 1 is connected to two injection molding units $2_1$ and $2_2$ which are provided separate from one another, so that the plasticated formulation passes from extruder 1 into injection units $2_1$ and $2_2$. Injection units $2_1$ and $2_2$ are advantageously charged via a two-way valve 5 to which the plasticated formulation is fed from extruder 1 and which distributes the plasticated formulation to the two injection units $2_1$ and $2_2$. It is moreover possible, depending on the further design of the apparatus, for the injection units 2 to be charged simultaneously or alternately. The feed valve 5 should have switching times which are as short as possible.

In the embodiment described here, the injection units 2 are plunger injection units. In a plunger injection unit there is an injection plunger inside an injection cylinder. The injection plunger pushes against the plasticated formulation present in the injection cylinder so that it can emerge through the outlet orifice of the injection unit 2 and enter a mold.

It is advantageous for the volume of the cylinder of an injection unit 2 to correspond to the volume of the mold 3 to be charged by the injection unit 2 or, if a plurality of molds 3 is to be charged in an injection process, to the volume of these molds 3. This means that active ingredient-containing formulation is no longer present in the injection unit 2 after each injection process.

Each injection unit 2 is able to inject a defined formulation volume into at least one mold 3. In the embodiment shown in FIG. 1, one mold $3_1$ and $3_2$ is provided for each of the injection units $2_1$ and $2_2$. It is possible in this case for the plasticated formulation first to enter injection unit $2_1$ via the feed valve 5. If injection unit $2_1$ is completely filled, the plasticated formulation continuously produced by extruder 1 can enter the second injection unit $2_2$ via the feed valve 5. During this, the first injection unit $2_1$ injects the formulation present therein into the mold $3_1$. When the injection process of the first injection unit $2_1$ is complete, i.e. when the first injection unit $2_1$ is able to receive a defined formulation volume again, advantageously the filling of the second injection unit $2_2$ is just complete, so that it is possible immediately thereafter to fill the first injection unit $2_1$ again.

It is accordingly possible for extruder 1 to be operated continuously and to be decoupled by feed valve 5 from the injection units 2 which operate only discontinuously.

In another embodiment, the mold 3 belonging to an injection unit 2 consists of a plurality of individual molds $3_1$ to $3_n$ arranged in parallel. In an injection process, the formulation is injected by the injection unit 2 simultaneously into the individual molds $3_1$ to $3_n$ arranged in parallel. It is additionally possible for the mold to consist of a plurality of molds $3_1$ to $3_n$ which can be coupled individually to the injection unit 2 and into which the formulation can be injected successively. It is advantageous for this purpose to provide an automatically operated exchange device which couples the individual molds $3_1$ to $3_n$ successively to the injection unit 2 assigned to them.

It is also possible for one mold 3 to be provided in each case for a plurality of injection units 2 and for it to be coupled alternatingly to the injection units 2. This embodiment was intended to be used when the melt plasticiation in extruder 1 is the rate-determining step.

Figure 3:
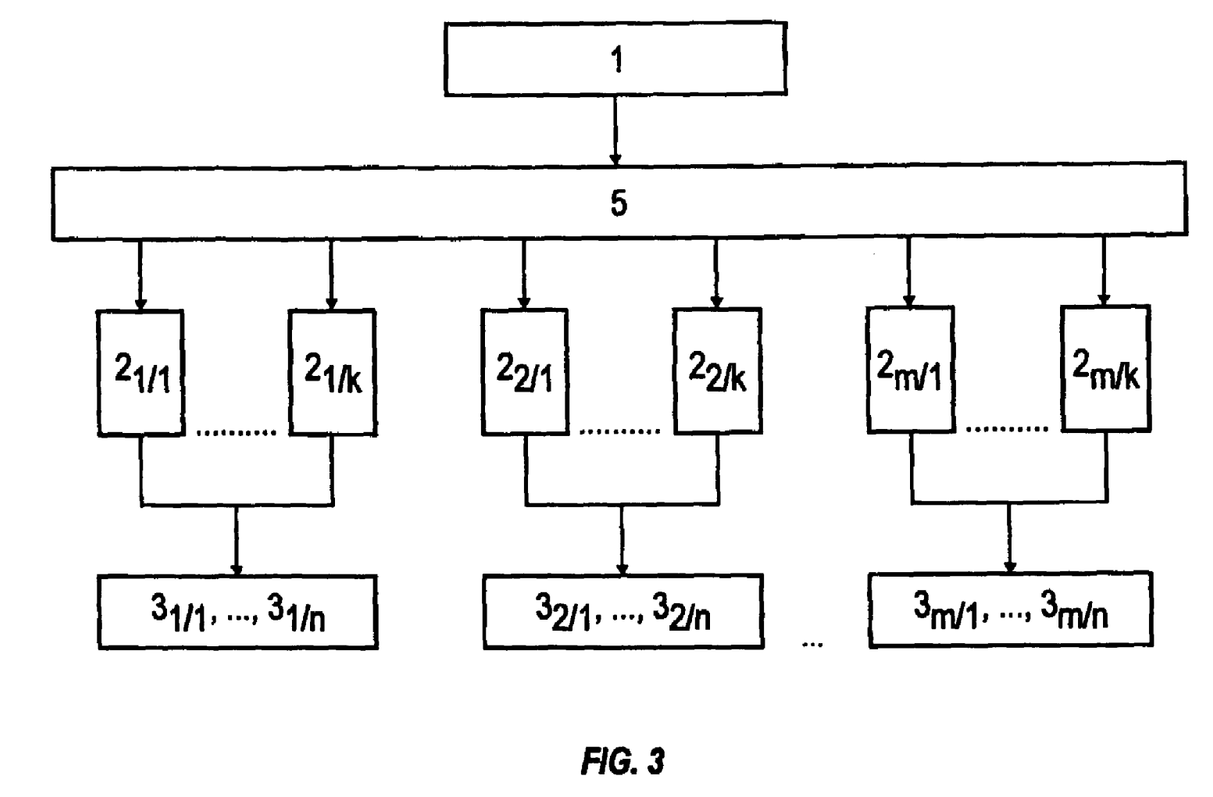
FIG. 3 shows the embodiment shown in FIG. 1 in a more general design.

FIG. 3 shows another embodiment of the apparatus according to the invention, which is a generalization of the embodiment shown in FIG. 1. In this embodiment, extruder 1 is connected to an m$\otimes$k-fold feed valve 5. This feed valve 5 distributes the formulation continuously produced in extruder 1 to m$\otimes$k injection molding units 2. The designation of the injection units 2 in FIG. 3 is such that the index k indicates the quantity of injection units 2 which charge a mold 3 or a group of molds. The index m indicates the number of groups of injection units which charge the m molds 3 or groups of molds. In addition, the index n designates how many molds 3 within a group of molds are assigned to a group of injection molding units 2 with a given index m. The indices m, k and n are, of course, integers greater than 1. It is further true for this embodiment of the apparatus according to the invention that m+k>2 is always complied with. This means that at least two injection molding units 2 must be provided.

In this more general embodiment of the apparatus according to the invention, the m$\otimes$k-fold feed valve 5 is able, like the embodiment explained with reference to FIG. 1, to fill the injection units 2 successively. However, it is also possible in addition for all injection units 2 or specifically selected quantities of these injection units 2 to be filled simultaneously. The chosen mode of filling depends, for example, on the rate at which extruder 1 plasticates the formulation, the volume of the forms produced in the molds 3 and the rate at which the formulation cools in the molds 3.

Figure 2:
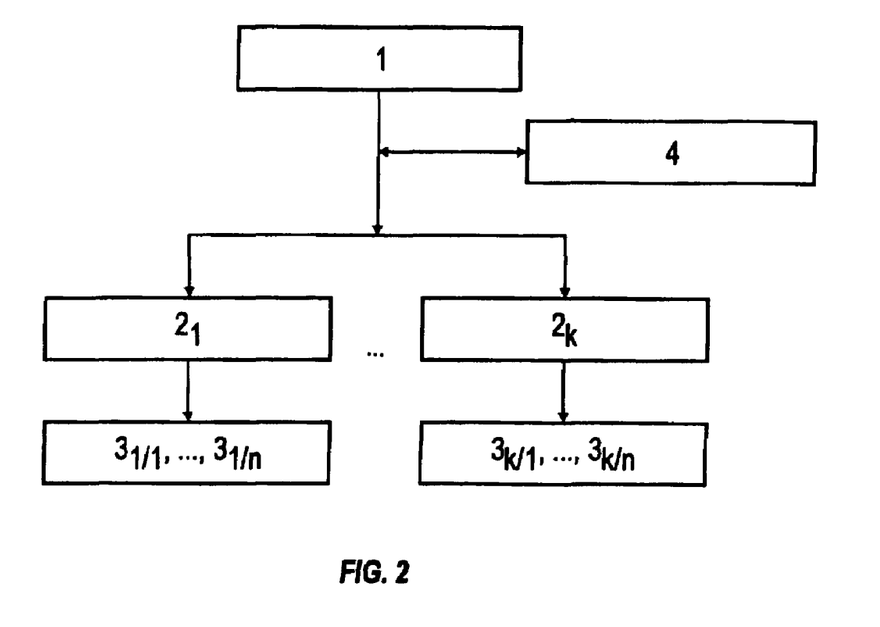
FIG. 2 shows another embodiment of the apparatus according to the invention, in which an accumulator unit 4 is disposed between the extruder 1 and the injection unit 2.

A further development of the embodiment explained above of the apparatus according to the invention is shown in FIG. 2. In this embodiment, a branch is provided in the connection of extruder 1 to one or more injection molding unit(s) 2 and leads to an accumulator unit 4. It is, of course, additionally possible to provide the feed valve 5 between extruder 1 and the injection units 2. However, this is not absolutely necessary. The accumulator unit 4 also serves to decouple the extruder 1, which is advantageously operated continuously, from the injection units 2 which can be operated only discontinuously. The accumulator unit 4 can temporarily store the formulation plasticated during an injection process and then convey the temporarily stored formulation gently and quickly to one of or to the injection units 2. For this purpose, the accumulator unit 4 also advantageously has a conveying unit.

In the specific case of the example shown in FIG. 2, the index k equals 1, i.e. an extruder 1 is provided with only one injection unit 2. It is possible in this case, although extrusion takes place continuously and the injection unit 2 operates discontinuously, for the apparatus to be operated continuously because of the storage of the melt in the accumulator unit 4.

Figure 4:
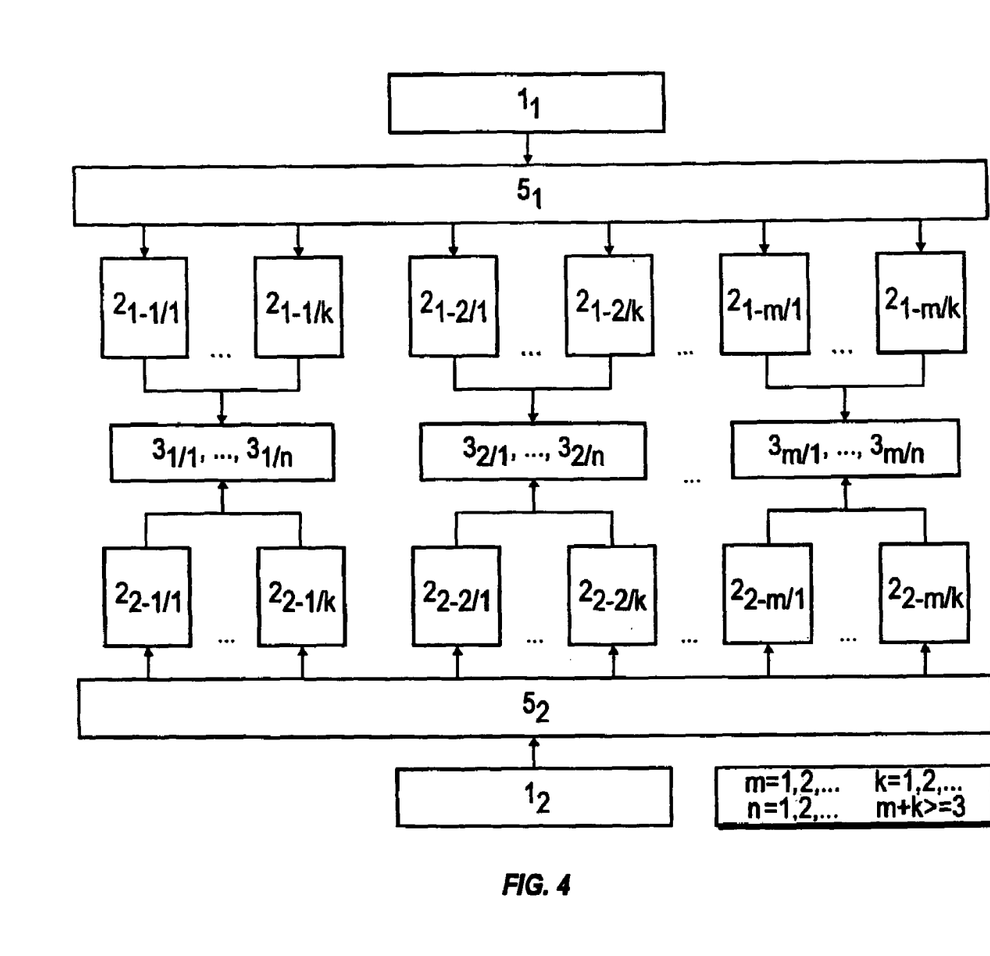
FIG. 4 shows another embodiment of the apparatus according to the invention.

In another embodiment of the apparatus according to the invention, the latter has a plurality of extruders 1 for processing different compositions, at least one composition being an active ingredient-containing formulation. FIG. 4 shows an example of this embodiment with two extruders 11 and 12. Each of the two extruders 11 and 12 are connected to injection units $2_1$ and $2_2$ respectively. The injection units $2_1$ and $2_2$ are also connected to molds 3. The design of a unit belonging to an extruder 1 is identical to the embodiment with one extruder 1 which is explained above with reference to FIG. 3 or FIG. 2. The embodiment shown in FIG. 4 of the apparatus according to the invention has a mold 3 connected to at least two injection units $2_1$ and $2_2$, to which compositions are fed from different extruders 11 and 12. It is thus possible with an apparatus in this embodiment to carry out a multicomponent injection molding. It is thus possible to produce multicomponent shaped articles such as, for example, directly enteric-coated tablets, multiply coated tablets, multilayer tablets with, for example, a multiphase release profile or forms with a 0 order release profile. It is characteristic of forms of this type that the active surface area of the form remains constant during dissolution of the form and thus the amount of active ingredient released per unit time does too. A 0 order release profile resulting therefrom is depicted in FIG. 4a. Possible forms with a 0 order release profile have already been described by W. D. Rhine et al., in "Controlled Release of Bioactive Materials", Academic Press, 1980, ISBN 0-12-074450-3.

The active ingredient-containing form to be produced may be, for example, essentially hemispherical with a concavity in the middle of the planar side of the hemisphere (i.e. have the shape of a hemisphere with a cavity) or half of a thick-walled hollow sphere. The form to be produced may also be a hollow hemicylinder. In order to obtain a release profile which is as nearly linear as possible, the forms should be produced by the multilayer process so that the active ingredient can be released only through the inner walls of the hollow half shapes, as described in the aforementioned article by W. D. Rhine et al.

Figure 5:
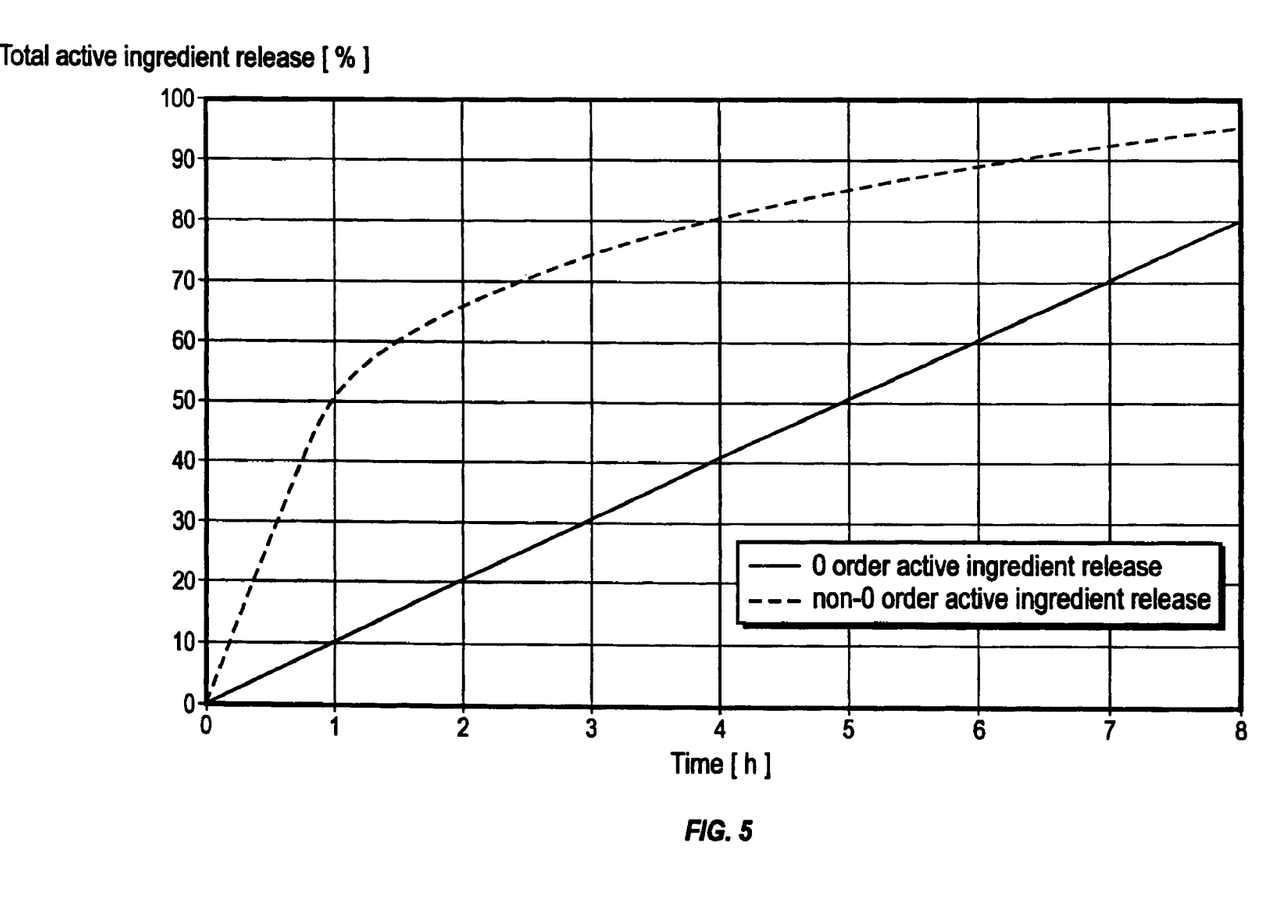
FIG. 5 shows an example of a hot runner system and FIG. 6 shows the PVT measurement of a verapamil formulation.

In another preferred embodiment of the apparatuses according to the invention explained above, the injection units and the molds are connected by hot runner systems, whose use is associated with both a higher yield and an increase in the production rate, because there is no sprue which also solidifies in conventional injection molding and usually determines the cycle time. Use of hot runner systems considerably increases the efficiency of the process especially for injection molding processes in which the amount of sprue is a very high percentage of the total composition and cannot be reused as raw material, because of the multiple exposure to heat, and for which large numbers of items are required (e.g. production of tablets). FIG. 5 shows such a hot runner system. The plasticated formulation enters a hot runner 10 at reference number 11 and exits at 12 from the hot runner nozzles 7 of the hot runner system in order to reach the molds 3. In the particularly preferred embodiment shown in FIG. 5, the temperature is controlled by a fluid which enters the hot runner 10 at reference number 8a and exits at reference number 8b. In addition, the temperature-controlled fluid for the hot runner nozzles 7 enters at reference number 9a and exits at reference number 9b. The formulation reaches the molds 3 via the injection runners 6 which are provided in the hot runner nozzles 7.

Temperature control of the hot runner system by means of a heating-cooling fluid has the advantage that the heat produced by compression and internal friction during the injection process can be removed very efficiently. It is moreover impossible with this temperature control by means of a heating-cooling fluid, in contrast to electrical heating, in which temperatures which are too high are set up in regions located close to electrical heating elements, for there to be local overheating of the formulation and thus harming of the active ingredients present in the formulation. For this reason, it is advantageous for the temperature of the injection units 2, of the outlet orifice of the extruder 1 and of the feed valve 5 also to be controlled by use of a heating-cooling fluid.

If the temperature of the hot runner system is controlled by an electrical heating system, the hot runner system can be provided with a suitable countercooling to allow better removal of the heat produced by compression and internal friction and thus avoid overheating and possible harm to the active ingredient present in the formulation.

The use of a hot runner system means that the active ingredient-containing forms are, after cooling, ejected without the appendages of the cooled formulation which have remained in the injection runner, because the formulation can be kept in the injection runner 6, through the control of the temperature thereof, at a temperature which prevents solidification of the formulation and thus connection to the cooled active ingredient-containing form.

Controlling the temperature of the hot runner system by means of a heating-cooling fluid or electrically with countercooling makes it possible to prevent the temperature of the formulation increasing because of internal effects such as, for example, compression or internal friction. Such an increase in temperature may lead to decomposition of ingredients of the active ingredient-containing formulation.

Controlling the temperature of the hot runner system by means of a heating-cooling fluid additionally makes it possible to prevent local overheating of the formulation.

The temperature of the hot runner system according to the invention is normally between 50 and 250° C., but is mostly between 100 and 200° C.

The formulation experiences an increase in temperature $\Delta T$ due to compression. The increase in temperature $\Delta T$ is calculated by the following formula:

$$\Delta T = \frac{\alpha T}{\varrho c_p} \Delta p,$$

where $\alpha$ is the isobaric volumetric expansion coefficient, T is the temperature of the formulation, $\rho$ is the density, $c_p$ is the specific heat capacity under constant pressure and $\alpha p$ is the sudden increase in pressure on adiabatic compression. The values for $\alpha$ and $\rho$ at a particular processing pressure and a particular processing temperature can be taken from, for example, pVT diagrams.

EXAMPLE

Figure 6:
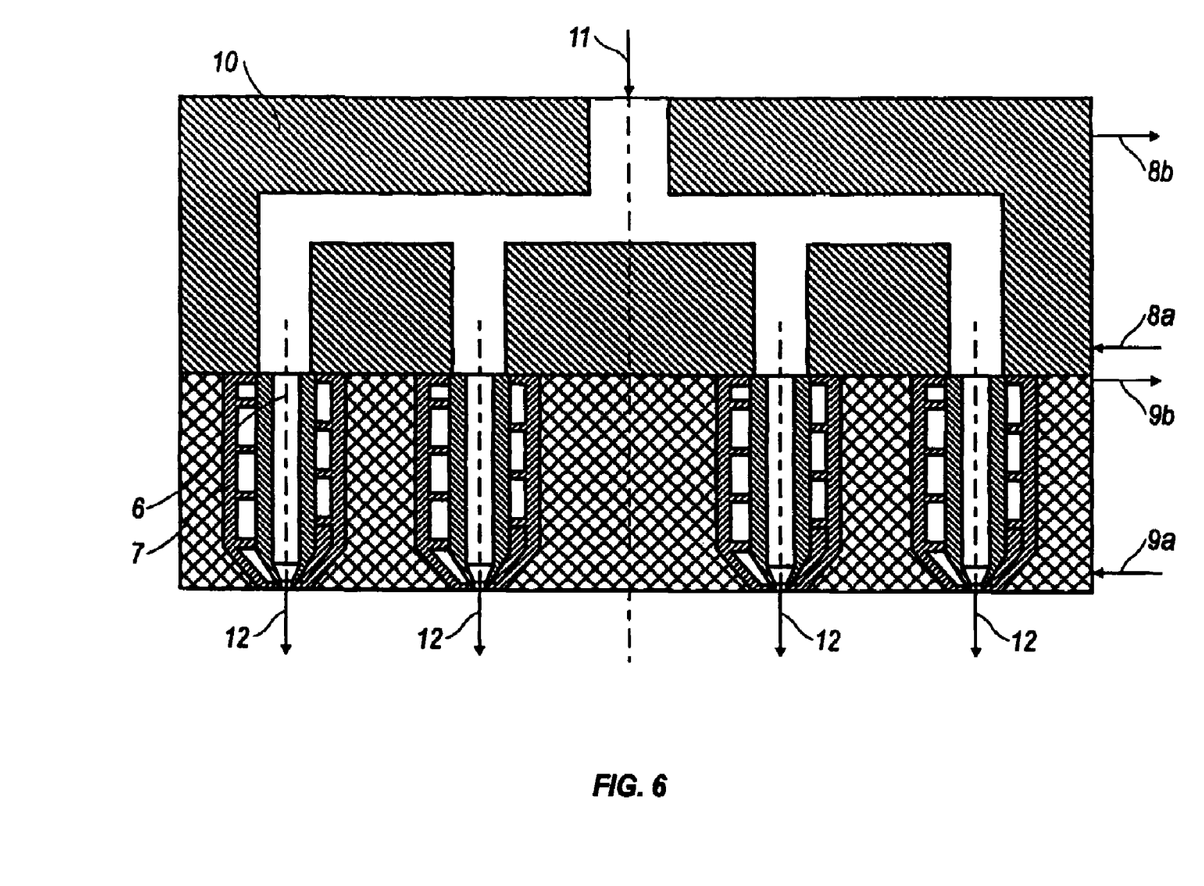
Figure 7:
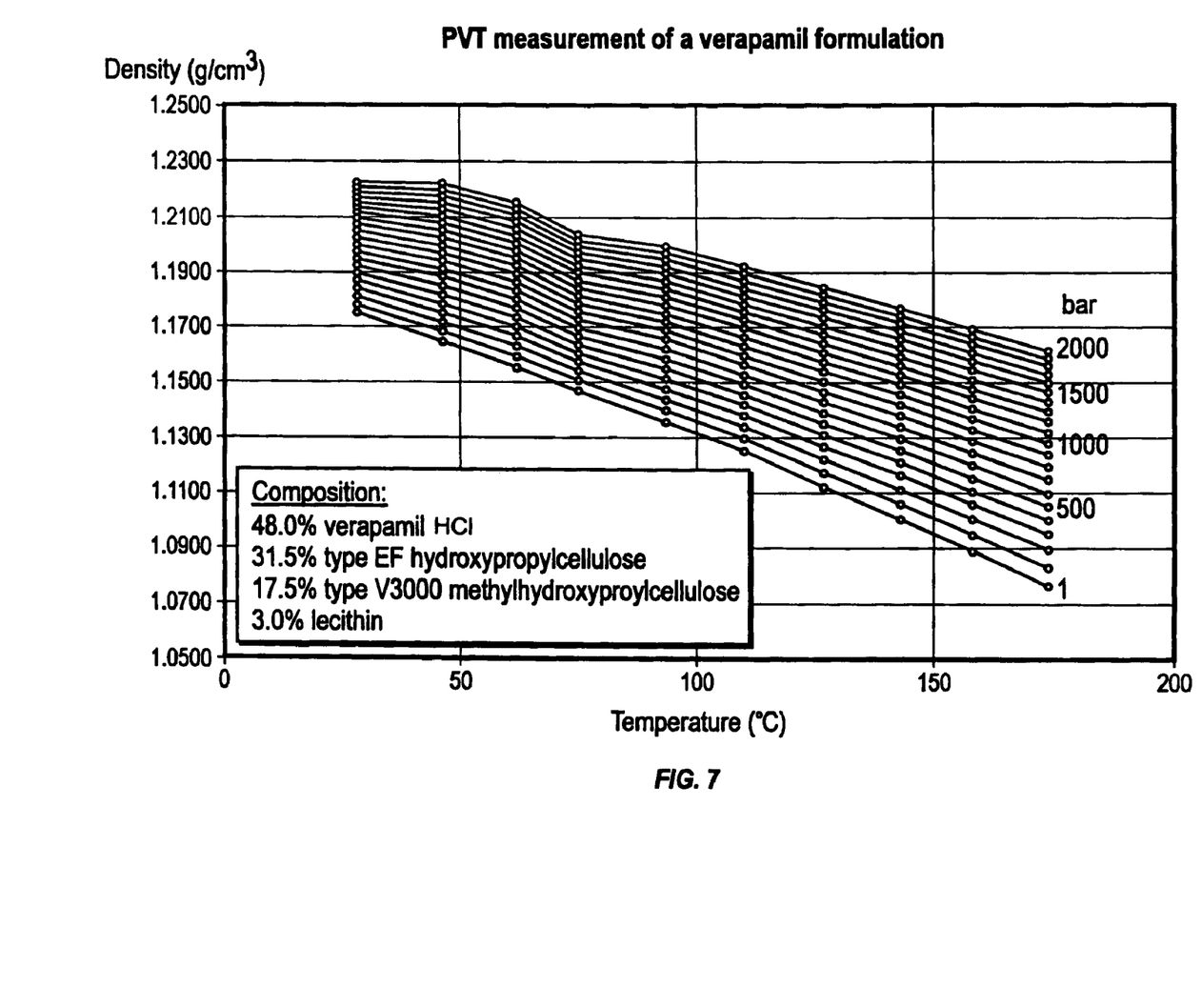

Compression of a melt consisting of 48.0% verapamil HCl, 31.5% type EF hydroxypropylcellulose, 17.5% type V3000 methylhydroxypropylcellulose and 3.0% lecithin from $1\times10^5$ Pa to $1.4\times10^8$ Pa results, with $\alpha=6.466\times10^{-4}$ K$^{-1}$, $\rho=1115$ kg/m$^3$ (values from the pVT diagrams for the above verapamil formulation shown in FIG. 6) and $c_p=2406$ J kg$^{-1}$ K$^{-1}$ at a processing temperature of T=126° C., in an increase in the melt temperature of $\Delta T=13.5°$ C.

The plasticated formulation experiences a further increase in temperature due to flow processes during flow into the cavities of the mold because of internal friction. Neglecting heat exchange across the walls of the melt feed system, the average increase in temperature $\Delta \overline{T}$ in the nozzle/gate system NG is calculated by $$\Delta \overline{T} = \frac{\Delta p_{NG}}{\varrho c_p}$$

EXAMPLE

On processing of the verapamil formulation mentioned above at a processing temperature of T=126° C. and with $\alpha P_{NG}=1.399\times10^8$ Pa, $\rho=1115$ kg/m$^3$ and $c_p=2406$ J kg$^{-1}$ K$^{-1}$, the above formula results in an increase in the melt temperature of $\Delta T=52.1°$ C.

Such increases in temperature of the formulation lead to the active ingredient in many formulations being harmed. If the formulation is distributed by a hot runner system to the individual cavities of the mold, harming of the active ingredient by an increase in temperature caused by compression and internal friction in the hot runner can be prevented by using the particularly preferred control of the temperature of the hot runner system according to the invention by means of a heating-cooling fluid, or by an electrically heated hot runner system with countercooling, because the heat produced can be removed efficiently. It is additionally possible to avoid local overheating in the formulation by controlling the temperature by means of a heating-cooling fluid.

An example of a process for producing a solid active ingredient-containing form from an active ingredient-containing formulation is indicated below. The apparatus shown in FIG. 1 is used for carrying out the process. The extruder 1 used in this case was the Werner & Pfleiderer ZSK 25 twin screw extruder. The injection molding units 2 were plunger injection units whose temperature was controlled by a heating-cooling fluid. The molds $3_1$ and $3_2$ were in each case a 4-fold single mold with mold body. The closure units used for the molds were Arburg 270 S units (without plasticating and injection unit).

The verapamil formulation (48.0% verapamil HCl. 31.5% type EF hydroxypropylcellulose, 17.5% type V3000 methylhydroxypropylcellulose, 3.0% lecithin) was used for the active ingredient-containing forms.

The melt temperature was 126° C., the cycle time was 9 s, the injection pressure was 1400 bar, the individual weight per molded article was 430 mg and the throughput through extruder 1 was 1.38 kg/h. The melt was distributed to the two molds $3_1$ and $3_2$ in each case by a hot runner system which was equipped in each case with four hot runner nozzles with heated injection runner.

While the test was being carried out, samples were taken of the produced molded articles and their content of verapamil HCl and decomposition products was determined by HPLC (high performance liquid chromatography). The results are summarized in the following table:

|  | Content of verapamil HCl [%] | Content of decomposition product 1 (rRT = 0.56) [%] | Content of decomposition product 2 (rRT = 1.46) [%] |
| --- | --- | --- | --- |
| Sample 1 | 47.8 | 0.01 | <0.01 |
| Sample 2 | 47.4 | 0.02 | <0.01 |

The values show that there was no major harm to the active ingredient either through the plastication in the twin screw extruder or through the injection molding process.

In addition, the crystallinity of the samples was determined by DSC (differential scanning calorimetry).

|  | Crystallinity [%] |
| --- | --- |
| Sample 1 | 0 |
| Sample 2 | 0 |

The results of the DSC measurements show that the active ingredient is 100% in the form of a molecular dispersion in the matrix.

It is to be noted that previously described configurations of embodiments of the invention can also be used in combination with other embodiments of the invention.

We claim:

1. A process for producing solid active ingredient-containing forms from an active ingredient-containing formulation which comprises at least one polymeric binder, in which the active ingredient-containing formulation is continuously plasticated, the plasticated formulation is temporarily stored and then the plasticated formulation is fed into an injection unit ($2_1$), the formulation present in this injection ($2_1$) is injected into a mold (3) and, during this, plasticated formulation is fed into another injection unit ($2_2$), and the formulation present in the other injection unit ($2_2$) is injected into the mold (3) or another mold the temperature of the plasticated formulation is controlled by a hot runner system comprising injection runners, wherein the hot runner system has a fluid or an electrical heating with counter-cooling for controlling the temperature of the injection runners (6).

2. A process as claimed in claim 1, wherein the volume of formulation fed into one injection unit (2) corresponds to the volume injected into the mold (3).

3. A process as claimed in claim 1, wherein two sheets are placed in the mold (3) before the injection, between which the formulation is injected.

4. The process of claim 1 wherein the solid active ingredients are pharmaceuticals.

* * * * *